United States Patent
Lim et al.

(10) Patent No.: US 10,611,720 B2
(45) Date of Patent: Apr. 7, 2020

(54) COMPOSITION FOR PREVENTING OR TREATING HAIR LOSS INCLUDING BENZENE DIAMINE DERIVATIVE

(71) Applicants: UNIST(ULSAN NATIONAL INSTITUTE OF SCIENCE AND TECHNOLOGY), Ulsan (KR); SEOUL NATIONAL UNIVERSITY HOSPITAL, Seoul (KR)

(72) Inventors: Mi Hee Lim, Ulsan (KR); Sang Tae Kim, Seoul (KR); Ho Seong Han, Seoul (KR)

(73) Assignees: UNIST (ULSAN NATIONAL INSTITUTE OF SCIENCE AND TECHNOLOGY), Ulsan (KR); Seoul National University Hospital, Seoul (KR)

(*) Notice: Subject to any disclaimer, the term of this patent is extended or adjusted under 35 U.S.C. 154(b) by 0 days.

(21) Appl. No.: 15/885,345

(22) Filed: Jan. 31, 2018

(65) Prior Publication Data
US 2019/0092717 A1    Mar. 28, 2019

(30) Foreign Application Priority Data

Sep. 26, 2017  (KR) .......................... 10-2017-0124526

(51) Int. Cl.
*C07D 213/53* (2006.01)
*C07C 211/51* (2006.01)
*C07C 233/43* (2006.01)
*A61P 17/14* (2006.01)

(52) U.S. Cl.
CPC ............ *C07C 211/51* (2013.01); *A61P 17/14* (2018.01); *C07C 233/43* (2013.01); *C07D 213/53* (2013.01)

(58) Field of Classification Search
CPC ... C07C 211/51; C07C 233/43; C07D 213/53; A61P 17/14
USPC ................ 544/124; 546/329; 514/235.5, 357
See application file for complete search history.

(56) References Cited

U.S. PATENT DOCUMENTS

2015/0272939 A1* 10/2015 Yan ..................... C07D 401/06
514/338

FOREIGN PATENT DOCUMENTS

WO   WO00/56710    9/2000

OTHER PUBLICATIONS

Beck et al., Minor Structural Variations of Small Molecules Tune Regulatory Activities toward Pathological Factors in Alzheimer's Disease, ChemMedChem, 12, pp. 1828-1838 (Oct. 9, 2017).*
Clavel et al., "Sox2 in the Dermal Papilla Niche Controls Hair Growth by Fine-Tuning BMP Signaling in Differentiating Hair Shaft Progenitors," *Dev. Cell*, 23(5): 981-994, 2012.
Clavel et al., "Sox2 in the Dermal Papilla Niche Controls Hair Growth by Fine-Tuning BMP Signaling in Differentiating Hair Shaft Progenitors," *Dev. Cell* (Author manuscript), 23(5): 981-994, 2012.
Cui, Daizong et al., "The Comparative Study on the Rapid Decolorization of Azo, Anthraquinone and Triphenylmethane Dyes by Anaerobic Sludge," Int. J. Environ. Res. Public Health, 13(11), 18 pgs. (Oct. 2016).
Geldenhuys, Werner J., et al., "Identification of multifunctional small molecule-based reversible monoamine oxidase inhibitors," *Med. Chem. Commun.*, 2:1099-1103 (Sep. 2011).
Office Action for Republic of Korean Application No. 10-2017-0124526, dated Dec. 28, 2018.
Panahi, Farhad et al., "Synthesis of a Novel Magnetic Reusable Organocatalyst Based on 4-Dialkylaminopyridines for Acyl Transformations," *ChemistrySelect*, 1(13):3541-3547 (Aug. 2016).
Peisino, Lucas E., et al,, "Iterative double cyclization reaction by $S_{RN}1$ mechanism. A theoretical interpretation of the regiochemical outcome of diazaheterocycles," *RSC Adv.*, 5:36374-36384 (Apr. 2015).

* cited by examiner

*Primary Examiner* — Deepak R Rao
(74) *Attorney, Agent, or Firm* — Klarquist Sparkman, LLP (57) ABSTRACT

Provided are a compound represented by the following Formula I, or a solvate, stereoisomer, or pharmaceutically acceptable salt thereof, and a composition for preventing or treating hair loss, the compound including the compound as an active ingredient:

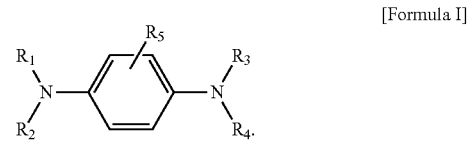

[Formula I]

3 Claims, 9 Drawing Sheets

COMPOSITION FOR PREVENTING OR TREATING HAIR LOSS INCLUDING BENZENE DIAMINE DERIVATIVE

CROSS-REFERENCE TO RELATED APPLICATION

This application claims the benefit of Korean Patent Application No. 10-2017-0124526, filed on Sep. 26, 2017, in the Korean Intellectual Property Office, the disclosure of which is incorporated herein in its entirety by reference.

BACKGROUND

1. Field

The present disclosure relates to a benzene diamine derivate, or a solvate, stereoisomer, or pharmaceutically acceptable salt thereof, and a composition for preventing or treating hair loss including the same as an active ingredient.

2. Description of the Related Art

Hair has a cycle of anagen, catagen, and telogen phases, and repeats growth and loss according to this cycle. In general, hair loss refers to abnormal loss of a large number of hairs due to a decrease in the number of hairs in the anagen phase and an increase in the number of hairs in the catagen or telogen phase.

The cause of hair loss is represented by genetic factors, and there are many other factors such as aging, stress, diseases, medications, UV, etc. Hair loss commonly occurs in men due to genetic factors, but it also frequently occurs in women due to various causes.

Natural extracts or herbal medicines have been widely used as drugs for the treatment of hair loss. However, their effects have not been fully elucidated, and their mechanism of action has not been clarified yet. Therefore, their range of application is ambiguous, and the nature of natural extracts and herbal medicines makes them difficult to standardize. Accordingly, there is a limitation in using natural extracts and herbal medicines as drugs, and most of them are only used as therapeutic aids such as quasi drugs or cosmetics.

Compounds approved by the USFDA for the treatment or prevention of hair loss are minoxidil and finasteride. However, the mechanism of action of minoxidil on hair growth has not been clarified, and minoxidil can only be used externally due to its toxicity. Finasteride is for oral use only and known to affect male hormones. Because of teratogenic effects which may be caused by only skin contact, finasteride is contraindicated for use in women of childbearing age. Accordingly, there is a demand for a drug that may replace these drugs for the prevention and treatment of hair loss.

SUMMARY

An aspect provides a compound represented by the following Formula I, or a solvate, stereoisomer, or pharmaceutically acceptable salt thereof:

[Formula I]

Another aspect provides a composition for preventing or treating hair loss, the composition including the compound, or the solvate, stereoisomer, or pharmaceutically acceptable salt thereof.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

An aspect provides a compound represented by the following Formula I, or a solvate, stereoisomer, or pharmaceutically acceptable salt thereof:

[Formula I]

wherein $R_1$ and $R_2$ are each independently hydrogen, a substituted or unsubstituted $C_1$-$C_6$ alkyl group, —$(CH_2)_n$-A, —$COR_6$, or —$COOR_6$;

$R_3$ and $R_4$ are each independently hydrogen, a substituted or unsubstituted $C_1$-$C_6$ alkyl group, —$COR_6$, or —$COOR_6$, or $R_3$ and $R_4$ together form a substituted or unsubstituted $C_3$-$C_{10}$ cycloalkyl group or a substituted or unsubstituted $C_2$-$C_{10}$ heterocycloalkyl group;

$R_5$ is selectively and independently hydrogen, a halogen, a hydroxy group, a substituted or unsubstituted amine, a substituted or unsubstituted $C_1$-$C_6$ alkyl group, or a substituted or unsubstituted $C_1$-$C_6$ alkoxy group;

A is a substituted or unsubstituted $C_2$-$C_{10}$ heterocycloalkyl group or a substituted or unsubstituted $C_2$-$C_{10}$ heteroaryl group;

n is an integer of 0 to 3;

$R_6$ is hydrogen or a substituted or unsubstituted $C_1$-$C_6$ alkyl group; and a substituent is selected from the group consisting of a halogen, a $C_1$-$C_6$ linear or branched alkyl group, a $C_1$-$C_6$ alkoxy group, a hydroxy group, an amine, a $C_1$-$C_6$ alkylamine group, a nitro group, an amide, a $C_1$-$C_6$ alkylamide, urea, and an acetyl group.

The 'alkyl' refers to linear or branched aliphatic hydrocarbon group having a particular number of carbon atoms, and it may be a methyl, ethyl, n-propyl, isopropyl, butyl, isobutyl, or t-butyl group.

The 'halogen' may be F, Cl, Br, or I.

The 'alkoxy' may be methoxy, ethoxy, n-propoxy, isopropoxy, n-butoxy, isobutoxy, or t-butoxy.

The 'heteroaryl' or 'heterocycloalkyl' refers to aryl or cycloalkyl including one or more heteroatoms selected from B, N, O, S, P(=O), Si, and P, and it may be specifically furyl, thiophenyl, thiazolyl, thiadiazolyl, isothiazolyl, oxadiazolyl, tetrazinyl, furazanyl, pyridyl, azetidinyl, acridinyl, benzodioxolyl, benzodioxanyl, benzofuranyl, carbazolyl, cinnolinyl, dioxolanyl, pyridyl, pteridinyl, purinyl, quinazolinyl, qunioxalinyl, quinolinyl, isoquinolinyl, tetrazolyl, imidazolyl, tetrahydroisoquinolinyl, pyrrolyl, piperonyl, pyrazinyl, pyrimidinyl, pyridazinyl, pyrazolyl, oxazolyl, oxazolinyl, triazolyl, indanyl, isoxazolyl, isoxazolidinyl, decahydroisoquinolyl, benzofuranyl, isobenzofuranyl, benzimidazolyl, benzothiazolyl, benzoisothiazolyl, benzooxazolyl, isoindolyl, indolyl, indazolyl, quinolyl, cinnolinyl, quinazolinyl, quinoxalinyl, carbazolyl, phenanthrinyl, benzodioxolyl, phenylpiperidinyl, tetrahydropuryl, tetrahydropyranyl, piperazinyl, homopiperazinyl, piperidyl, piperidopiperidyl, morpholinyl, thiomorpholinyl, piperidonyl, 2-oxopiperazinyl, 2-oxopiperidinyl, pyrrolidinyl, 2-oxopyrrolidinyl, or oxazolidinyl.

The 'cycloalkyl' may be selected from cyclopropyl, cyclobutyl, cyclopentyl, cyclohexyl, cyclooctyl, cycloheptyl, perhydronaphthyl, adamantly, crosslinked cyclic groups, and spirobicyclic groups.

The 'solvate' refers to the compound of the present disclosure or a salt thereof including a stoichiometric or non-stoichiometric amount of a solvent bound by non-covalent intermolecular forces. Preferred solvents may be solvents which are non-volatile, non-toxic, and suitable for administration to humans.

The 'stereoisomer' refers to those having the same chemical or molecular formula as, but optically or sterically different from, the compounds of the present disclosure or salts thereof, and it may be specifically a diastereoisomer, an enantiomer, a geometrical isomer, or a conformational isomer.

In a specific embodiment, in the compound, or the solvate, stereoisomer, or pharmaceutically acceptable salt thereof, any one or more of $R_1$ and $R_2$ are hydrogen, —$(CH_2)_n$-A, or —$COR_6$.

In a specific embodiment, in the compound, or the solvate, stereoisomer, or pharmaceutically acceptable salt thereof, any one or more of $R_3$ and $R_4$ are hydrogen, a substituted or unsubstituted $C_1$-$C_6$ alkyl group, or —$COR_6$, or $R_3$ and $R_4$ together form a substituted or unsubstituted $C_2$-$C_{10}$ heterocycloalkyl group.

In a specific embodiment, A may be a substituted or unsubstituted heterocycloalkyl group or a substituted or unsubstituted heteroaryl group. A may be specifically selected from the group consisting of and * indicates a binding site with a neighboring atom.

In a specific embodiment, A may be a substituted or unsubstituted pyridine. Here, the substituent may be selected from the group consisting of halogen, a $C_1$-$C_6$ linear or branched alkyl group, a $C_1$-$C_6$ alkoxy group, a hydroxy group, an amine group, a $C_1$-$C_6$ alkylamine group, a nitro group, an amide group, a $C_1$-$C_6$ alkylamide group, urea, and an acetyl group.

In a specific embodiment, any one or more of $R_1$ and $R_2$ may be hydrogen, a pyridylmethyl group, or an acetyl group.

In a specific embodiment, the pyridylmethyl may be a 2-pyridylmethyl group. The 2-pyridylmethyl group means and * indicates a binding site with a neighboring atom.

In a specific embodiment, any one or more of $R_3$ and $R_4$ may be hydrogen, a methyl group, or an acetyl group, or $R_3$ and $R_4$ together may form In a specific embodiment, the compound may be a compound represented by the following Formula, or a solvate, stereoisomer, or pharmaceutically acceptable salt thereof:

Another aspect provides a composition for preventing or treating hair loss, including any one compound of the above-described compounds, or a solvate, stereoisomer, or pharmaceutically acceptable salt thereof.

Another aspect provides a method for preventing, treating, or improving hair loss, comprising administrating any one compound of the above-described compound, or the solvate, stereoisomer, or pharmaceutically acceptable salt thereof to a subject in need thereof.

The 'pharmaceutically acceptable salt' refers to a salt which has effective action relatively non-toxic and harmless to patients, and whose side effects do not degrade the beneficial efficacy of the compound in the composition of the present disclosure. The pharmaceutically acceptable salt refers to any organic or inorganic addition salt of the compound. The salt may use an inorganic acid and an organic acid as a free acid. The inorganic acid may be hydrochloric acid, bromic acid, nitric acid, sulfuric acid, perchloric acid, phosphoric acid, etc. The organic acid may be citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid, malonic acid, etc. In addition, these salts include alkali metal salts (sodium salts, potassium salts, etc.) and alkaline earth metal salts (calcium salts, magnesium salts, etc.). For example, the acid addition salt may include acetate, aspartate, benzoate, besylate, bicarbonate/carbonate, bisulfate/sulfate, borate, camsylate, citrate, edisilate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salt, etc., and among them, hydrochloride or trifluoroacetate may be used.

The composition may be administered to a subject via various routes in order to prevent or treat hair loss. The subject may be a mammal, for example, a human, a cow, a horse, a pig, a dog, a sheep, a goat, or a cat, and the mammal may be a human. An administration dose of the compound of the present disclosure effective for the human body may vary depending on age, body weight, and sex of a patient, administration mode, health conditions, and disease severity.

The administration may be performed by various formulations for oral administration or parenteral administration such as intravenous, intraperitoneal, transdermal, intradermal, subcutaneous, epithelial, rectal, inhalation, nasal, sublingual, or intramuscular administration. In a specific embodiment, the administration may be oral administration or external application. Formulations may be prepared by using a diluent or an excipient such as a filler, an extender, a binder, a wetting agent, a disintegrant, a surfactant, etc., which is commonly used.

In a specific embodiment, the composition may be for oral administration. A solid formulation for oral administration may include tablets, pills, powder, granules, fine granules, capsules, suspensions, oral solutions, rapidly dispersing tablets, syrups, chewable tablets, troches, etc. Such solid formulations may be prepared by mixing one or more of the compound of the present disclosure with at least one excipient, for example, starch, calcium carbonate, sucrose, lactose, gelatin, etc. In addition to simple excipients, lubricants such as magnesium stearate or talc may also be used. As a liquid formulation for oral administration, suspensions, liquids for internal use, emulsions, syrups, etc. may be used. In addition to simple diluents that are frequently used, such as water or liquid paraffin, various excipients, for example, wetting agents, sweeteners, fragrances, preservatives, etc. may be included.

In a specific embodiment, the composition may be for parenteral administration. Formulations for parenteral administration may include sterilized aqueous solutions, injectable formulations, non-aqueous solvents, suspensions, emulsions, lyophilized formulations, aerosols, nasal administration, emulsions, suppositories, etc. For the non-aqueous solvent or suspension, propylene glycol, polyethylene glycol, vegetable oils such as olive oil, or injectable esters such as ethyloleate may be used. For a base material of suppositories, witepsol, macrogol, tween 61, cacao butter, laurin butter, glycerol, gelatin, etc. may be used.

In a specific embodiment, the composition may be for external application. External preparations may be applied in a form of a patch, a band, an emulsion, an ointment, a pack, a gel, a cream, a lotion, a liquid, or a powder. As a cosmetic, a skin softener, a nutrient lotion, a massage cream, a nutrient cream, a moisturizing cream, a functional cream, a mist, a pack, a gel, or a skin adhesive-type formulation may be applied. Therefore, to be used for external application, ingredients commonly used in external preparations such as cosmetics or drugs, for example, an aqueous ingredient, an oily ingredient, a powdery ingredient, alcohols, a moisturizing agent, a thickener, an UV absorbing agent, a whitening agent, a preservative, an antioxidant, a surfactant, a flavoring agent, a colorant agent, several skin nutrition agents, etc. may be properly blended with the composition, as needed. The external preparations may be properly blended with a sequestering agent, such as disodium edetate, trisodium edetate, sodium citrate, sodium polyphosphate, sodium metaphosphate, gluconic acid, etc., a drug, such as caffeine, tannin, verapamil, licorice extract, glabridin, a hot water extract of fruit of carlin, various crude drugs, tocopherol acetate, glycyrrhizic acid, tranexamic acid and their derivatives or salts, vitamin C, magnesium phosphate ascorbate, glucoside ascorbate, albutin, kojic acid, and sugars such as glucose, fructose, trehalose, etc.

Still another aspect provides a health functional food for preventing or improving hair loss, including any one compound of the above-described compounds, a solvate, stereoisomer, or health functional food-acceptable salt thereof.

When the compound of the present disclosure may be included in a health functional food, the compound may be added as it is or used together with other health functional foods or health functional food ingredients according to a common method. A mixing amount of the active ingredient may be determined according to the purpose of use. Generally, the active ingredient constituting the composition according to the present disclosure may be included in an amount of 0.01% by weight to 15% by weight, preferably 0.2% by weight to 10% by weight, based on the total weight of the food. When prepared as a drink, the compound may be included in an amount of 0.1 g to 30 g, preferably 0.2 g to 5 g, based on 100 ml, and the entire drink may be composed of natural ingredients. However, for long-term intake for health control and hygiene, the amount may be below the above range. Since the active ingredient does not have any safety problems, it may be used in a larger amount than the above range.

The health functional food composition according to the present disclosure may be prepared as a common health functional food formulation known in the art. The health functional food may be prepared as, for example, a powder, a granule, a tablet, a pill, a capsule, a suspension, an emulsion, a syrup, an infusion, a liquid, an extract, a vitamin complex, a gum, a tea, a jelly, a beverage, etc., and preferably, as a beverage. As a food-acceptable carrier or additive, any carrier or additive which is known in the art to be applicable in the preparation of a desired formulation may be used. The health functional food may include nutrients, vitamins, electrolytes, flavors, sweeteners (e.g., stevia, rebaudioside A, glycyrrhizin, thaumatin, saccharin, aspartame, etc.), extenders (e.g., cheese, chocolate, etc.), colorants, pectic and salts thereof, alginic acid and salts thereof, organic acids, sugars (e.g., glucose, fructose, maltose, sucrose, dextrin, cyclodextrin, xylitol, sorbitol, erythritol, etc.), protective colloidal viscofiers, pH regulators, stabilizers, antiseptics, glycerin, alcohols, carbonators used in carbonated drinks, etc. according to the purpose or preference.

In addition, the health functional food may include pulp for preparing a natural fruit juice, a fruit juice beverage, or a vegetable beverage. Further, the health functional food composition may further include a food additive. The suitability of the "food additives" may be determined by the specification and standard of the concerned item in accordance with the General Provisions and General Test Methods of the Korea Food Additives Code authorized by the Korea Food and Drug Administration, unless otherwise specified.

A compound represented by Formula I, a solvate, stereoisomer, or pharmaceutically acceptable salt thereof according to an aspect may be used to treat a disease or symptom of a subject.

A composition including the compound represented by Formula I, the solvate, stereoisomer, or pharmaceutically acceptable salt thereof according to another aspect may be used to prevent, treat, or improve hair loss.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, the present invention will be described in more detail with reference to Examples. However, these Examples are for illustrative purposes only, and the scope of the invention is not intended to be limited by these Examples.

1. Example 1: Synthesis of Benzene Diamine Derivates

Benzene diamine derivates were synthesized as follows.

1-1. Synthesis of N$^1$-(pyridin-2-ylmethyl)benzene-1,4-diamine (Compound 1)

(1) Step 1

Under a nitrogen atmosphere, 1-fluoro-4-nitrobenzene, N,N-diisopropylethylamine, and DMF were put in a well-dried flask equipped with a reflux condenser and a magnetic stirrer, and then 2-(aminoethyl)pyridine was added at room temperature, and this mixture was heated at 70° C. 12 hours later, water was added to a resulting brown solution, and extracted with EtOAc. An extracted organic solution was washed with water and brine. Thereafter, MgSO$_4$ was added thereto, and filtration was performed, and then a filtrate was concentrated. This concentrated solution was purified by silica column chromatography to obtain a yellow solid compound (0.29 g, yield: 58%).

(2) Step 2

The compound obtained in Step 1, tris(acetylacetonato) iron (III), and ethanol were put in a well-dried flask equipped with a reflux condenser and a magnetic stirrer, and then mixed with hydrazine hydrate. This mixture was heated under reflux for 2 hours at 120° C. 2 hours later, when the reactants remained, 4 equivalents of hydrazine hydrate was further added every hour. Resulting brown oil was concentrated and purified by silica column chromatography. The purified compound was dissolved in a small amount of MeOH, and excess 5 M HCl was added thereto to produce a compound in the form of a salt. This product was concentrated under vacuum and then washed with $Et_2O$. This resulting compound was dissolved in water to produce an aqueous layer, which was washed with $Et_2O$, and concentrated to obtain a compound. This product was a light yellow solid (0.45 g. yield: 85%).

1-2. Synthesis of 4-morpholino-N-(pyridin-2-ylmethyl)aniline (Compound 2)

(1) Step 1

Morpholinoaniline in ethanol was put in a well-dried 2-neck flask equipped with a reflux condenser and a magnetic stirrer. The flask was purged with nitrogen for 5 minutes to ensure nitrogen atmosphere inside the flask. 1-methyl-imidazole-carboxaldehyde was put in the flask under nitrogen atmosphere, and heated under reflux at 95° C. for 30 minutes. 30 minutes later, a reaction was confirmed by TLC, and temperature of the flask was reduced to room temperature to stop the reaction. The obtained compound was concentrated under vacuum. This product had a brown solid phase (0.164 g. yield: 82%).

(2) Step 2

Prior to reaction, $NaBH_4$ and the compound obtained in Step 1 were dried under vacuum. The dried compound was put in a flask and dissolved in ethanol. To this mixed solution, $NaBH_4$ was added at 0° C. This mixed solution was stirred at 0° C. for 5 minutes. 5 minutes later, the flask was allowed to maintain at room temperature. Thereafter, water was added to the flask to produce precipitates. The resulting precipitates were filtered through a Büchner funnel, and repeatedly washed with water. A resulting yellow compound was dried under vacuum and recovered (0.108 g. yield: 35.8%).

1-3. Synthesis of $N^1,N^1$-dimethyl-1,4-phenylenediamine (Compound 3)

10% Pd/c was put in a well-dried 2-neck flask equipped with a magnetic stirrer. The flask was purged with nitrogen to ensure nitrogen atmosphere inside the flask. $N^1,N^1$-dimethyl-1,4-nitroaniline was dissolved in ethanol absolute, and the flask was purged with hydrogen. The flask was sufficiently purged with hydrogen until the air inside the flask was replaced by hydrogen, followed by stirring at room temperature for 24 hours. 24 hours later, Pd/c used as a catalyst was filtered and separated from the product by using Cellite, followed by washing with ethanol. Water was added to a resulting brown solution and extracted with EtOAc. An extracted organic solution was washed with water and brine again. Thereafter, $MgSO_4$ was added to the organic layer, followed by filtration. A filtrate was concentrated. A product had a brown solid phase (0.7 g, yield: 95%).

1-4. Synthesis of N-(4-dimethylamino)phenyleneacetamide (Compound 4)

-continued

Pyridine was put in a well-dried flask equipped with an ice bath and a magnetic stirrer, and then $N^1,N^1$-dimethyl-1,4-phenylenediamine was dissolved therein. The flask was purged with nitrogen for 5 minutes to ensure nitrogen atmosphere inside the flask. Acetic anhydride was added dropwise to the flask for 5 minutes. 5 minutes later, the temperature of the flask was maintained at room temperature for 30 minutes. 30 minutes later, water was added to a resulting black solution, which was extracted with DCM. The extracted organic solution was washed with water and brine. Thereafter, $MgSO_4$ was added to the solution, which was then filtered, and a filtrate was concentrated. A resulting compound had a black solid phase (0.5 g, yield: 47.5%).

1-5. Synthesis of N-(4-aminophenyl)acetamide (Compound 5)

N-(4-nitrophenyl)acetamide, tris(acetylacetonato)iron (III), and ethanol were put in a well-dried flask equipped with a reflux condenser and a magnetic stirrer, and then mixed with hydrazine hydrate. This mixture was heated under reflux for 1 hour at 120° C. A product was concentrated under vacuum and then purified by silica column chromatography. The resulting product was a light pink solid (0.45 g. yield: 92%).

1-6. Synthesis of N,N-(1,4-phenylene)diacetate Amide (Compound 6)

1,4-phenylenediamine and acetic anhydride were mixed in a well-dried flask equipped with a magnetic stirrer. This mixture was heated for 6 hours at 90° C. 6 hours later, iced water was added to the flask containing the reaction solution to produce precipitates. The precipitates were filtered and repeatedly washed with water and dilute hydrochloric acid. A compound obtained by drying under vacuum was a white solid (12.5 g, yield: 70%).

Compounds 1 to 6 thus obtained were freeze-dried to obtain dry powders. The obtained Compounds 1 to 6 were simply extracted with an aqueous solution, and dried to obtain dry powders.

A variety of benzene diamine derivates of the present disclosure may be prepared by a method well known to those skilled in the art, without being limited to the above-described Compounds 1 to 6.

2. Example 2: Measurement of Cell Viability by Using hDPC Cells

In order to examine effects of the benzene diamine derivates of the present disclosure on improvement of cell viability of hair follicular cells, human hair follicle dermal papilla cells (hDPCs) were treated with the benzene diamine derivates, and cell viability was examined. Oligomer Aβ generally has cytotoxicity, and the present inventors found that oligomer Aβ has cytotoxicity also in hair follicular cells. Therefore, examination was performed by using oligomer Aβ as a toxic material for hDPC.

In detail, $2\times10^3$ hDPCs were dispensed in a multi 96-well plate containing a DMEM medium supplemented with 10% FBS, and cultured in a $CO_2$ incubator (Thermo Scientific) at 37° C., 5% $CO_2$ for 24 hours. Thereafter, experiments were performed by using a normal group which was treated with only cells, a control group which was a group treated with 10 μl of 2 nM oligomer Aβ (oAβ) previously synthesized, and an experimental group which is prepared by treating the normal group with the same concentration of oligomer Aβ and 25 μg/ml of each benzene diamine derivate sample in water or DMSO. To examine cell viability at 72 hours after treatment of the cell line with the sample, 20 μl of 2% MTT solution was added to the cell culture medium. 3 hours later, to terminate the reaction, the culture medium was removed by aspiration, and 50 μl of DMSO was added. 30 minutes later, the reaction was terminated. Thereafter, OD value was measured at 570 nm by using a microplate reader (BioTek, Synergy HT, USA).

Figure 1:
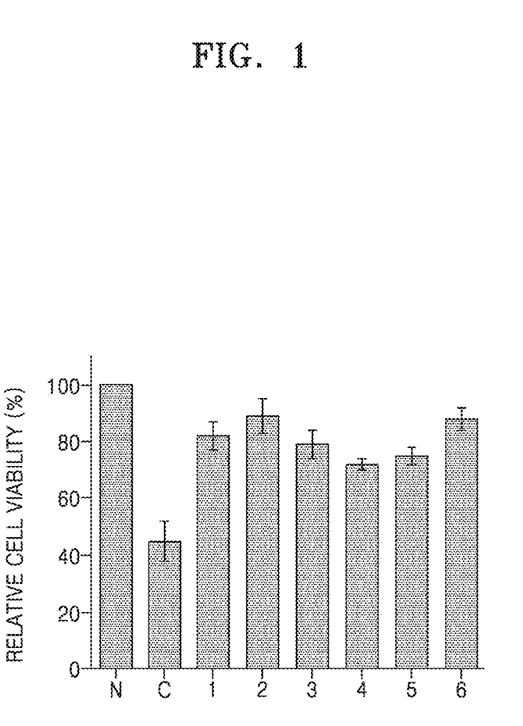
FIG. 1 shows cell viability which represents human hair follicle dermal papilla cell (hDPC) protective effects of Compounds 1 to 6 against oligomer Aβ-induced cytotoxicity.

As a result, it was observed that 50% or more of hDPC cells (C) treated with oligomer Aβ died. However, when each of Compounds 1 to 6 was treated, cell viability of 82±2%, 87±5%, 81±1%, 74±3%, 77±1%, or 86±1% was observed, as compared with the control group (N) (FIG. 1).

3. Example 3: Examination of Expression of Hair Growth Stimulating Factor in hDPC Cells In order to examine whether the benzene diamine derivates of the present disclosure actually exhibit the effect of improving hair loss by increasing expression of hair growth stimulating factors in hair follicular cells, hDPCs were treated with the benzene diamine derivate to examine SOX-9 and Cola17a1 expressions. As in Example 2, examination was performed by using oligomer Aβ as a cytotoxic material for hDPC.

Figure 2:
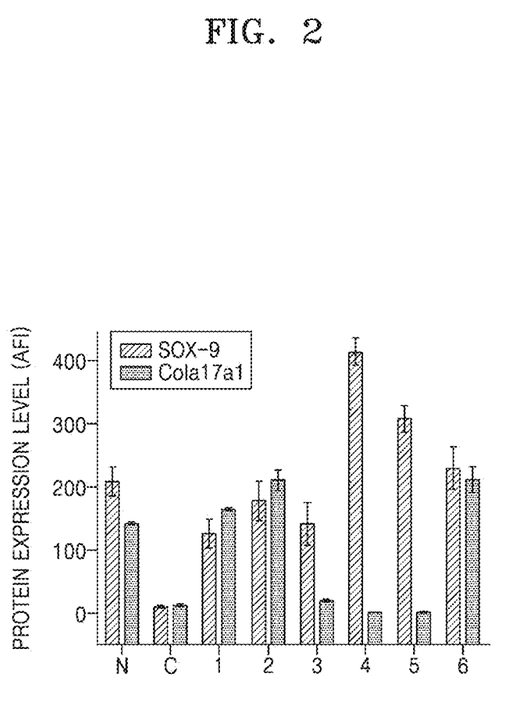
FIG. 2 shows changes in SOX-9 and Cola17a1 expression levels of hDPCs caused by Compounds 1 to 6 under an oligomer Aβ-induced cytotoxic environment.
Figure 3:
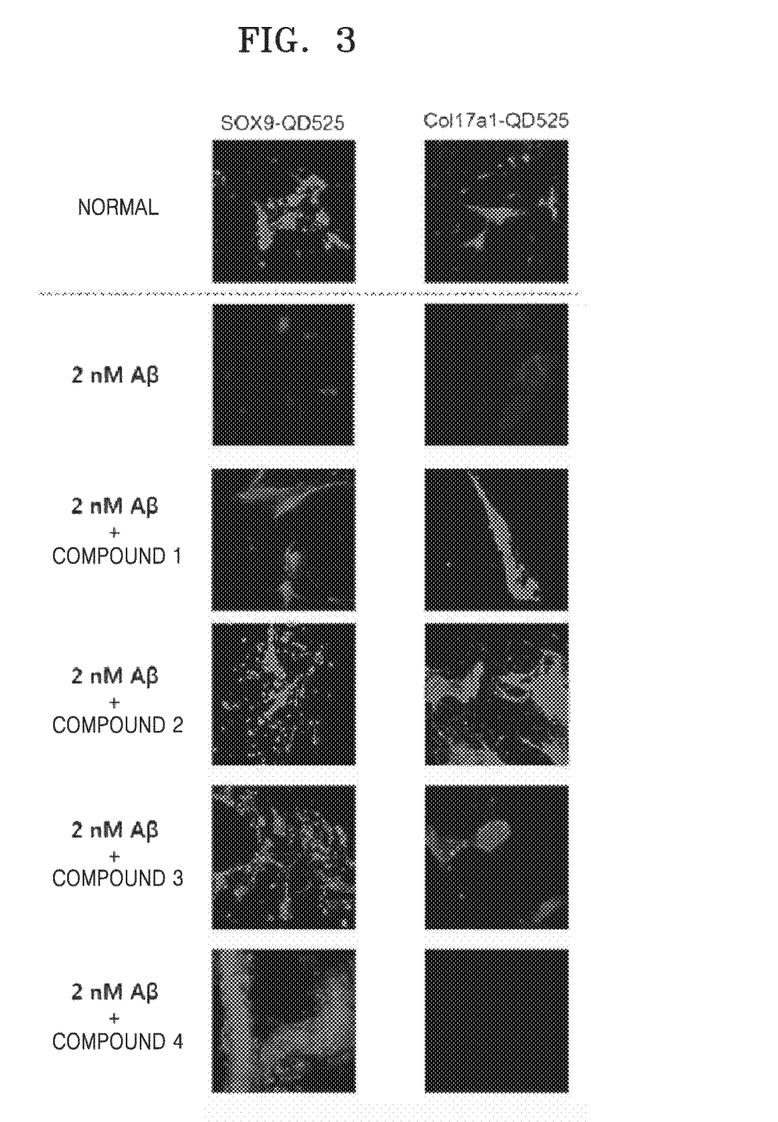
FIG. 3 is images showing changes in SOX-9 and Cola17a1 expression levels of hDPCs caused by Compounds 1 to 4 under the oligomer Aβ-induced cytotoxic environment.
Figure 4:
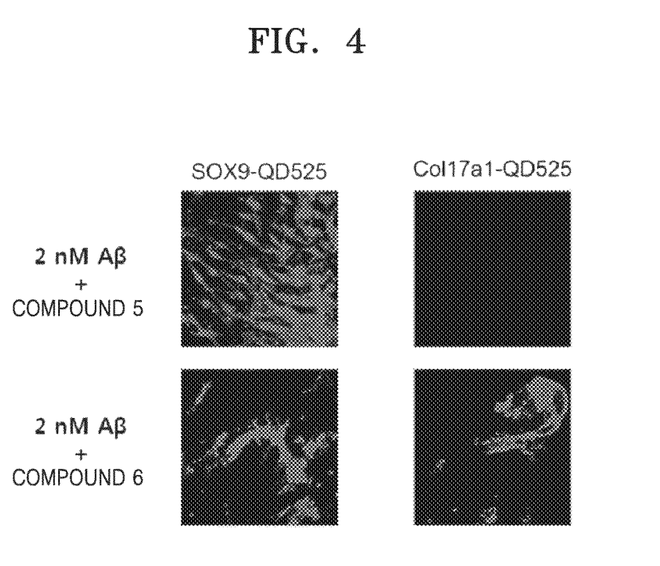
FIG. 4 is images showing changes in SOX-9 and Cola17a1 expression levels of hDPCs caused by Compounds 5 and 6 under the oligomer Aβ-induced cytotoxic environment.

In detail, hDPCs were dispensed in a 35 mm-confocal dish as the above culture, and a control group was treated with 10 μl of 2 nM of synthesized oligomer Aβ (oAβ) and an experimental group was prepared by treating the normal group with the same concentration of oligomer Aβ and 25 μg/ml of each benzene diamine derivate sample. At 3 days after treatment of the derivatives, the cells were fixed with 4% paraformaldehyde solution, and washed with PBS, and then fluorescence of ROI (relative fluorescence intensity) was measured at 488 nm by a confocal microscope (CONFOCAL, LSM710, Carl Zeiss, Germany) to examine SOX-9 and Cola17a1 expressions. As in Example 2, examination was performed by using oligomer Aβ as a cytotoxic material for hDPC. As a result, SOX-9 expression in hDPC cells was 220±12 AFI (average fluorescence intensity) in the normal group and 12±4 AFI in the cells (control group C) treated with the cytotoxic oligomer Aβ, indicating that SOX-9 expression was remarkably reduced, as compared with the normal cells (N). In contrast, when Compounds 1 to 6 were treated, respective compounds showed different patterns, but all compounds remarkably increased SOX-9 expression as high as 134±23 AFI, 187±23 AFI, 157±21 AFI, 446±110 AFI, 325±45 AFI, and 267±56 AFI, as compared with the cells treated with cytotoxic oligomer Aβ. COL17A1 expression was 143±11 AFI in the normal group and 16±6 AFI in the cells (control group C) treated with the cytotoxic oligomer Aβ, indicating that COL17A1 expression was remarkably reduced, as compared with the normal cells (N). In contrast, when Compounds 1 to 6 were treated, respective compounds showed different patterns, but all compounds remarkably increased COL17A1 expression as high as 152±13 AFI, 234±31 AFI, 24±6 AFI, 2±1 AFI, 3±1 AFI, and 226±34 AFI, as compared with the cells treated with cytotoxic oligomer Aβ (FIGS. 2 to 4).

4. Example 4: Expressions of SOX-9 and COL17A1 in hDPC Cells

It was examined whether the benzene diamine derivates of the present disclosure actually exhibit the effect of improving hair loss by increasing expressions of hair growth stimulating factors SOX9 and COL17A1 in hair follicular cells.

In detail, hDPCs were dispensed in a 35 mm-confocal dish as the above culture, and a control group was treated with 10 μl of 2 nM of the synthesized oligomer Aβ (oAβ) and an experimental group was prepared by treating the normal group with the same concentration of oligomer Aβ and 25 μg/ml of each benzene diamine derivate sample. At 3 days after treatment of the derivatives, the cells were fixed with 4% paraformaldehyde solution, and washed with PBS, and then fluorescence was measured at 488 nm/565 nm by a confocal microscope (CONFOCAL, LSM710, Carl Zeiss, Germany) to examine SOX-9 and Cola17a1 expressions. As in Example 2, examination was performed by using oligomer Aβ as a cytotoxic material for hDPC. As a result, SOX-9/QD525 was strongly expressed in normal hDPC cells, whereas weakly expressed in the cells (control group C) treated with the cytotoxic oligomer Aβ, indicating that SOX-9 expression was remarkably reduced by oligomer Aβ, as compared with the normal cells (N). In contrast, when Compounds 1 to 6 were treated, respective compounds showed different patterns, but all compounds remarkably increased SOX-9 expression, as compared with the cells treated with cytotoxic oligomer Aβ. In particular, Compounds 4 and 5 more strongly promoted the expression. COL17A1 expression was inhibited in the cells (control group C) treated with the cytotoxic oligomer Aβ, as compared with the normal group. That is, COL17A1 expression was remarkably inhibited by oligomer Aβ, as compared with the normal cells (N). All compounds remarkably increased COL17A1 expression, as compared with the cells treated with cytotoxic oligomer Aβ. In particular, treatment of Compounds 2 to 6 remarkably increased the expression. These results suggest that cytotoxic oligomer Aβ inhibits factors essential for the growth of hair follicle stem cells and adipose stem cells in the skin to exhibit function of inducing hair growth inhibition, leading to hair loss, but the benzene diamine derivates enhance expressions of SOX-9 and COL17A1 factors which stimulate hair growth (FIGS. 2 to 4).

5. Example 5: Examination of Hair Growth Change by Using Animal Models

In order to examine therapeutic effects of the benzene diamine derivates of the present disclosure on hair loss, APP/PS/Tau mouse which is a hair loss-induced mouse model was selected as a control group, and C57BL6 mouse was selected as a normal group. An experimental group was prepared by orally administering the control group with the benzene diamine derivate at a concentration of 100 μg/Kg/0.1 ml using a zonde twice a week, and then changes in appearance were observed.

In detail, APP/PS/Tau was purchased from Jackson lab (BAR HARBOR, USA), and APP/Tau female and APP/PSen1de9 purchased from Taconic (Hudson, USA) were cross-mated for 6 generations, and 4-month-old mouse models were obtained from F1. The mouse models were characterized by appearance of hair loss. The hair loss mouse models were divided into groups of 6 mice, and among the hair loss mouse models, the normal group and the control group were orally administered with a phosphate buffer carrier (PBS) for 2 months, and the experimental group was orally administered with 100 μl of $N^1$-(pyridin-2-ylmethyl)benzene-1,4-diamine (Compound 1) at a concentration of 100 μg/Kg twice a week for 2 months. Thereafter, changes in their appearance were compared.

Figure 5:
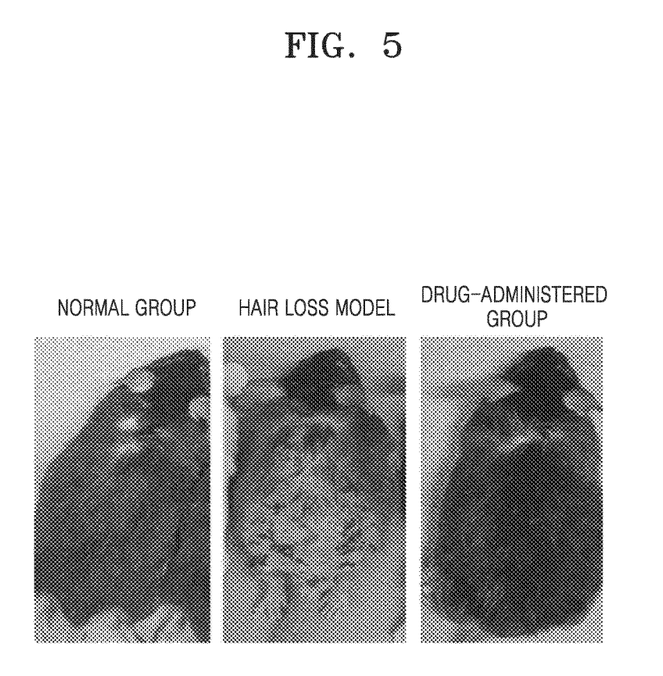
FIG. 5 shows changes in the skin of hair loss mouse models caused by Compound 1.

As a result, the control group showed bleeding, inflammation, and hair loss in the back skin, but the experimental group treated with the benzene diamine derivate showed remarkable improvement in hair loss, similar to the normal group (FIG. 5), suggesting that as in Example 4, the benzene diamine derivates inhibit production of reactive oxygen species induced by oligomer Aβ of the skin, inhibit suppression of SOX-9 expression in hair follicle stem cells, COL17A1 expression around hair follicles, and growth of adipose stem cells by NETOSIS caused by skin bleeding with inflammation, and also inhibit production of neutrophil elastase and aging or regression of hair follicle stem cells, leading to stimulation of hair follicle growth and promotion of hair growth.

6. Example 6: Examination of Changes of SOX-2 and SOX-9 Expressions in Hair Loss Models It was examined whether hair growth stimulating factors were expressed by the benzene diamine derivates of the present disclosure in the hair loss animal model of Example 5. In general, stratum corneum existing in the epidermis of the skin regularly slough off, and therefore, in order to make up stratum corneum, SOX-2 around the endothelial-dermal layer is a transcription factor essential for maintaining self-renewal or pluripotency of undifferentiated embryonic stem cells. SOX-2 is known to be critical for regulation of progenitor cells in hair growth (Dev Cell. 2012 Nov. 13; 23(5): 981-994). Dermal papilla cells (DP cells) are known to play a key role in inducing growth of hair follicles, and therefore, SOX-2 is an important contributor to normal DP function (Clavel et al., 2012). Further, growth of hair follicles is stimulated by stem cells in the anagen cycle, and during development of hair follicles, formation of hair follicle stem cells occurs, which requires the transcription factor, SOX-9. Therefore, SOX-9 plays a very important role in maintaining adult hair follicle stem cells.

Figure 6:
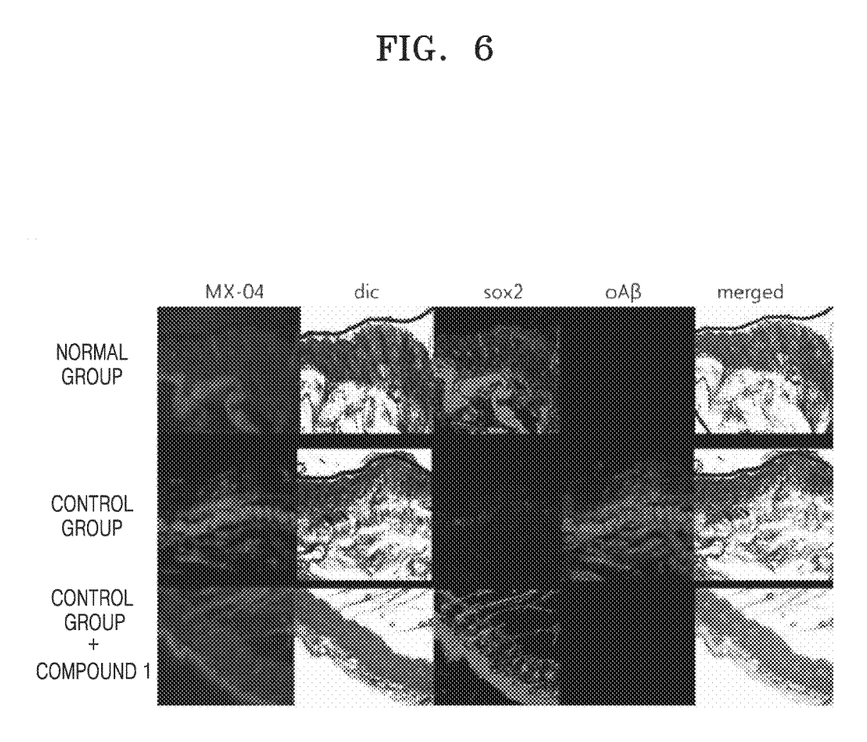
FIG. 6 shows SOX2 expression patterns after oral administration of Compound 1 to hair loss mouse models.
Figure 7:
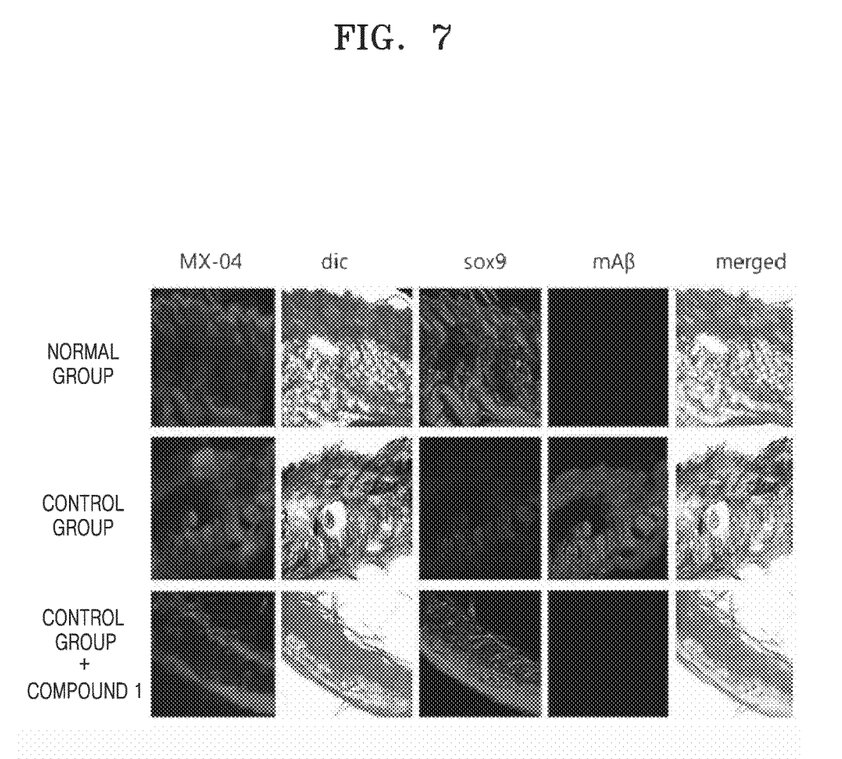
FIG. 7 shows SOX9 expression patterns after oral administration of Compound 1 to hair loss mouse models.

Accordingly, the present inventors examined whether expressions of hair growth stimulating factors, SOX-2 and SOX-9 were increased in hair loss animal models by the benzene diamine derivates of the present disclosure. In order to examine SOX-2 and SOX-9 expressions inside skin tissues, APP/PS/Tau mouse which is a hair loss-induced mouse model was selected as a control group and C57BL6 mouse was selected as a normal group, as in Example 5. An experimental group was prepared by orally administering the control group with the benzene diamine derivative at a concentration of 100 μg/Kg/0.1 ml using a zonde twice a week. 2 months later, incision of the skin was performed under local anesthesia, and the skin tissues were fixed in 4% paraformaldehyde solution for 24 hours, and fixed in a plastic mold with O.C.T. Compound (SAKURA, USA) for cryostat sectioning. Thereafter, the tissues were frozen in a freezer for 5 hours, and sectioned at a thickness of 5 μm by using a freezing microtome (LEICA, JAPAN), and SOX-2/QD525 which is a conjugate of an antibody against Sox-2 and a fluorescent dye, SOX-9/QD525 against Sox-9, and m/oAβ-cy5.5 antibody solution against skin oligomer Aβ were used in a 24-well plate to induce an antigen-antibody reaction. Thereafter, the plate was put on a slide glass and covered with a cover slide, and stored in a dark acrylic box, and fluorescence imaging was observed under a confocal microscope (LSM710, Carl Zeiss, Germany) by 405/488/565 nm laser. As a result, SOX-2 expression was observed in the skin of the normal group, but SOX-2 was not expressed in the control group. Remarkable expression of oligomer Aβ was observed, as compared with the normal group. However, in the hair loss model administered with Compound 1, SOX-2 was remarkably expressed close to the normal group (FIG. 6). Similarly, in the control group, SOX-9 was rarely expressed, but monomer/oligomer Aβ was expressed. In contrast, in the hair loss model APP/PS/Tau administered with Compound 1, SOX-9 expression was remarkably increased, similar to the normal group, but monomer/oligomer Aβ expression was decreased. In all the three groups, MXO4 which is a blue fluorescent dye detecting plaques in the blood vessel was strongly observed (FIG. 7), suggesting that Compound 1 inhibits oligomer Aβ production rather than removes plaques.

7. Example 7: Examination of Transdermal Absorption of Benzene Diamine Derivates It was examined whether transdermal absorption of the benzene diamine derivates of the present disclosure exhibits therapeutic effects on APP/PS/Tau hair loss mouse models, like in oral administration.

(1) Preparation of Formulation for Transdermal Administration

For preparation of formulations for transdermal administration, toluene was added to 5% by weight of $N^1$-(pyridin-2-ylmethyl)benzene-1,4-diamine (compound 1), 50% by weight of a polyethylene vinyl acetate adhesive, 10% by weight of glycerol monooleate, 5% by weight of triacetin, and 5% by weight of triethyl citrate and completely dissolved such that a total weight of solid was 65%. The drug-containing adhesive solution was coated on a silicone-treated polyester release film fixed on an applicator, and dried at 90° C. for 15 minutes at an air speed of 1500 rpm to prepare a sheet of an adhesive layer having a thickness of 100 μm, which was then bound to a polyester backing film. The resulting product was cut into a predetermined size to prepare a transdermal formulation.

(2) Transdermal Administration

Figure 8:
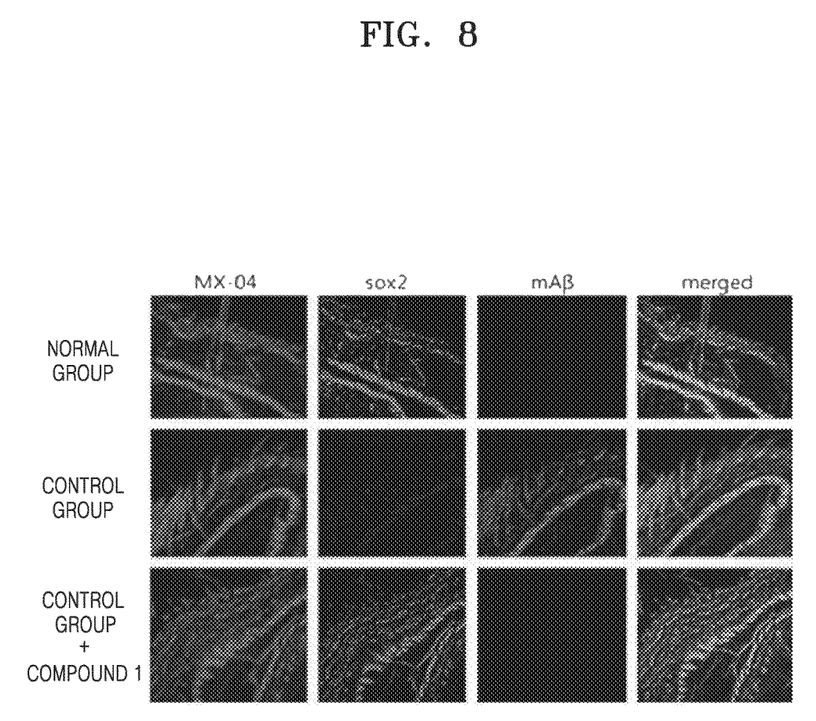
FIG. 8 shows SOX2 expression patterns after transdermal administration of Compound 1 to hair loss mouse models.
Figure 9:
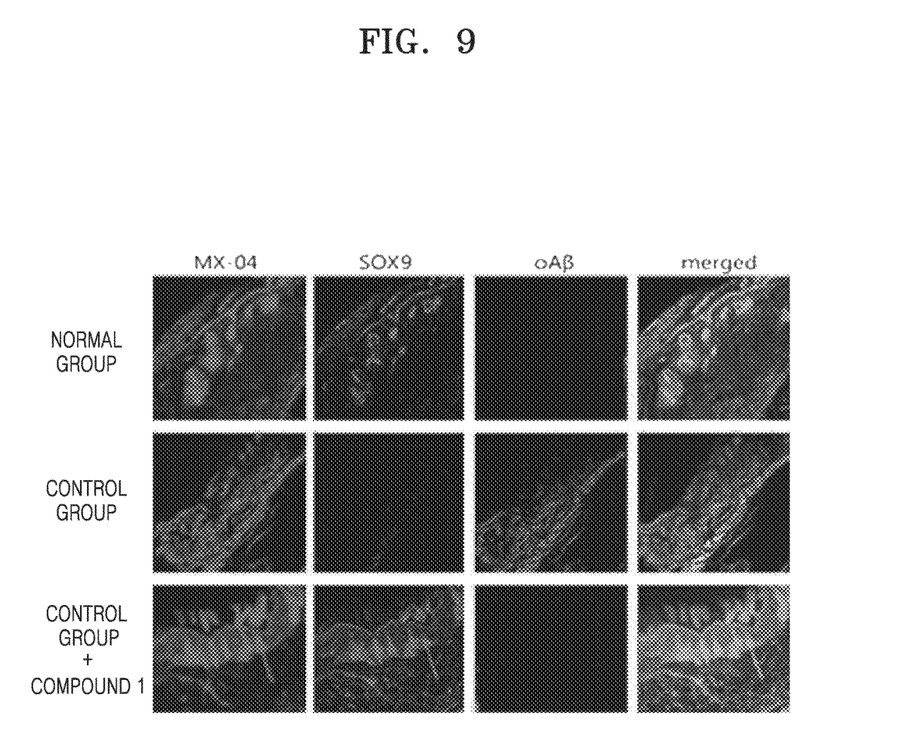
FIG. 9 shows SOX9 expression patterns after transdermal administration of Compound 1 to hair loss mouse models.

The transdermal formulation was attached to the back skin of the hair loss animal model APP/PS/Tau of Example 5, and replaced every 2 weeks for 2 months. Incision of the skin of the animal model was performed under local anesthesia, and the skin tissues were fixed in 4% paraformaldehyde solution for 24 hours, and fixed in a plastic mold with O.C.T. Compound (SAKURA, USA) for cryostat sectioning. Thereafter, the tissues were frozen in a freezer for 5 hours, and sectioned at a thickness of 5 μm by using a freezing microtome (LEICA, JAPAN). Then, SOX-2/QD525 which is a conjugate of an antibody against Sox-2 and a fluorescent dye, SOX-9/QD525 against Sox-9, and m/oAβ-cy5.5 antibody solution against skin oligomer Aβ were used in a 24-well plate to induce an antigen-antibody reaction. Thereafter, the plate was put on a slide glass and covered with a cover slide, and stored in a dark acrylic box, and fluorescence imaging was observed under a confocal microscope (LSM710, Carl Zeiss, Germany) by 405/488/565 nm laser. SOX-2 expression was observed in the skin of the normal group, whereas SOX-2 was not observed in the control group. Remarkable expression of oligomer Aβ was observed in the control group, as compared with the normal group. However, in the hair loss model administered with the transdermal formulation including Compound 1, SOX-2 was remarkably expressed, close to the normal group (FIG. 8). Similarly, in the control group, SOX-9 was rarely expressed, but oligomer Aβ was expressed. In contrast, when the transdermal formulation including Compound 1 was administered, SOX-9 expression was remarkably increased, similar to the normal group, but oligomer Aβ expression was decreased. In all the three groups, MXO4 which is a blue fluorescent dye detecting plaques in the blood vessel was strongly observed (FIG. 9), suggesting that Compound 1 inhibits oligomer Aβ production rather than removes plaques. Accordingly, since presence of skin aggregates was observed in epidermis, dermis, and endothelium of the normal group, the aggregate observed in the experimental group was originally a normal phenomenon, and SOX9 expression of hair follicle stem cells which affect the hair growth function of skin was strongly distributed. In contrast, in the hair loss mouse model, reactive oxygen species and neutrophil elastase (ELAN) which is secreted by neutrophils or macrophages during inflammation were increased in the skin tissue or blood vessel at the time point when monomer Aβ production increased, and as a result, skin connective tissues or tight junctions of elastin fibers were broken, and thus SOX9 expression in hair follicle stem cells in the skin tissue was reduced, and inflammation and hair loss were induced by increased reactive oxygen species. However, Compound 1-treated group inhibited inflammation, thereby inhibiting monomer Aβ production and inducing production of hair follicle stem cells, and consequently, skin regeneration and SOX9 expression of hair follicle stem cells were increased, resulting in hair growth efficacy. Further, it may be predicted that the increased absorption of Compound 1 in the skin tissue is possible not only by oral administration but also by transdermal administration (FIG. 9). As in the results of Example 5, in the hair loss models treated with the control group, SOX-2 was not expressed, whereas oligomer Aβ was remarkably expressed, as compared to the normal group. However, the transdermal formulation including Compound 1 showed remarkable SOX-2 expression, close to the normal group (FIG. 8). Similarly, SOX-9 was rarely expressed in the control group, whereas SOX-9 was remarkably expressed in the group attached with the transdermal formulation including Compound 1, closed to the normal group (FIG. 9). Accordingly, it can be seen that the benzene diamine derivate of the present disclosure may be used for external application as well as for oral administration.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method for treating, or improving hair loss, comprising administrating a compound represented by the following formula, or a solvate, stereoisomer, or pharmaceutically acceptable salt thereof to a subject in need thereof:

2. The method of claim 1, wherein the administrating is an oral administration.

3. The method of claim 1, wherein the administrating is an external application.

* * * * *